(12) United States Patent
Mitomo et al.

(10) Patent No.: US 8,804,108 B2
(45) Date of Patent: Aug. 12, 2014

(54) INSPECTION METHOD AND INSPECTION APPARATUS

(75) Inventors: Kenji Mitomo, Hitachinaka (JP); Kenji Oka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 252 days.

(21) Appl. No.: 13/202,727

(22) PCT Filed: Dec. 4, 2009

(86) PCT No.: PCT/JP2009/006615
§ 371 (c)(1),
(2), (4) Date: Nov. 2, 2011

(87) PCT Pub. No.: WO2010/113232
PCT Pub. Date: Oct. 7, 2010

(65) Prior Publication Data
US 2012/0050729 A1 Mar. 1, 2012

(30) Foreign Application Priority Data
Mar. 31, 2009 (JP) .................................. 2009-084001

(51) Int. Cl.
*G01N 21/00* (2006.01)
(52) U.S. Cl.
USPC ...................................................... 356/237.1
(58) Field of Classification Search
CPC ................. G01N 21/84–21/958; G01N 21/00
USPC ..................................................... 356/237.1
See application file for complete search history.

(56) References Cited

U.S. PATENT DOCUMENTS

| 5,377,001 | A  | * | 12/1994 | Malin et al. ................. 356/237.2 |
| 5,377,002 | A  | * | 12/1994 | Malin et al. ................. 356/237.2 |
| 7,016,028 | B2 | * | 3/2006  | Holsteyns et al. .......... 356/237.1 |
| 7,038,773 | B2 | * | 5/2006  | Kuhlmann et al. ......... 356/237.4 |
| 7,869,024 | B2 | * | 1/2011  | Urano et al. ................ 356/237.2 |

(Continued)

FOREIGN PATENT DOCUMENTS

| JP | 09-115973 A   | 5/1997 |
| JP | 2008-020359 A | 1/2008 |

OTHER PUBLICATIONS

Notification of Reasons for Refusal issued Dec. 4, 2012 in Japanese Patent Application No. 2009-084001.

(Continued)

*Primary Examiner* — Roy M Punnoose
(74) *Attorney, Agent, or Firm* — McDermott Will & Emery LLP

(57) ABSTRACT

This application relates to an inspection apparatus including: a stage which holds a specimen; an illumination optical system which illuminates a surface of the specimen held on the stage, with illumination light; a dark-field optical system which detects scattered light generated by the illumination light with which the specimen is illuminated; a photoelectric converter which converts the scattered light detected by the dark-field optical system, into an electric signal; an A/D converter which converts the electric signal obtained by conversion by the photoelectric converter, into a digital signal; a judgement unit which determines the dimension of a foreign substance on the surface of the specimen on the basis of a magnitude of the scattered light from the foreign substance; and a signal processor which determines an inspection condition by use of information on the scattered light from the specimen surface.

16 Claims, 10 Drawing Sheets

(56) References Cited

U.S. PATENT DOCUMENTS

| | | | |
|---|---|---|---|
| 8,101,935 B2* | 1/2012 | Takahashi et al. | 250/559.4 |
| 8,260,035 B2* | 9/2012 | Tek et al. | 382/152 |
| 2004/0235206 A1* | 11/2004 | Kuhlmann et al. | 438/14 |
| 2004/0246472 A1* | 12/2004 | Holsteyns et al. | 356/237.1 |
| 2008/0075353 A1* | 3/2008 | Tek et al. | 382/145 |
| 2009/0073440 A1* | 3/2009 | Tiemeyer | 356/338 |
| 2009/0140180 A1* | 6/2009 | Takahashi et al. | 250/559.45 |

OTHER PUBLICATIONS

Japanese Office Action issued in correpsonding Japanese Application No. 2013-012765, dated Feb. 12, 2014, with English translation.

* cited by examiner

FIG. 2A  Side View
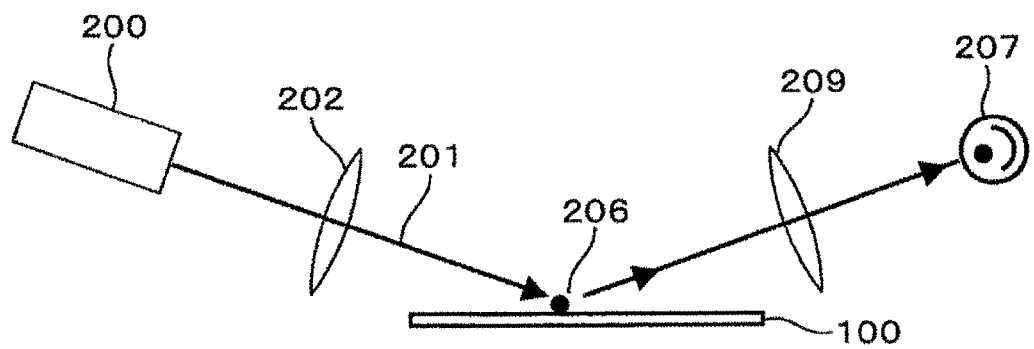
FIG. 2B  Plan View
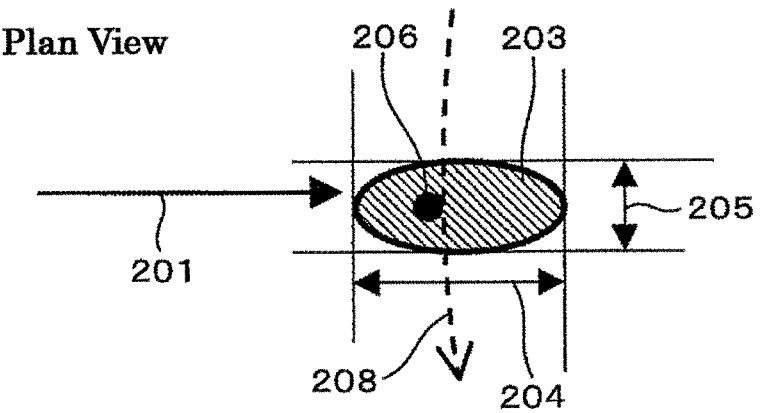

INSPECTION METHOD AND INSPECTION APPARATUS

RELATED APPLICATIONS

This application is the U.S. National Phase under 35 U.S.C. §371 of International Application No. PCT/JP2009/006615, filed on Dec. 4, 2009, which in turn claims the benefit of Japanese Application No. 2009-084001, filed on Mar. 31, 2009, the disclosures of which Applications are incorporated by reference herein.

TECHNICAL FIELD

The present invention relates to an inspection method and an inspection device, for example, a method and a device for inspecting a surface of an inspection object such as a semiconductor wafer for defects.

BACKGROUND ART

For example, in the manufacturing processes of semiconductor devices, circuits are formed by pattern transfer to bare wafers and etching. In manufacturing processes of various semiconductor devices for circuit forming, foreign substances adhered to wafer surfaces, defects existing on wafer surfaces, and the like are major factors of reducing yields. The foreign substances adhered to wafer surfaces and the defects existing on wafer surfaces are controlled in each manufacturing process, where the foreign substances adhered to bare wafer surfaces, the defects existing on the wafer surface, and the like can be detected by a surface inspection apparatus with high sensitivity and high throughput.

The methods for inspecting wafer surfaces for foreign substances and defects can be roughly classified into the methods using a charged-particle beam such as an electron beam and the methods using light, and the methods using light include the methods of taking an image of the wafer surface by use of a camera and analyzing the image information and the methods of detecting with a light receiving element the light scattered by the wafer surface and analyzing the magnitude of the light scattering. The Patent Literature 1 discloses an example of the latter methods, and the Patent Literature 2 discloses a technique related to the present invention. That is, the Patent Literature 2 discloses a method enabling detection of small defects foreign substances or the like on inspection objects having great of surface conditions, by producing a margin in the dynamic range of an amplifier by DC (direct current) offset removal and increasing the gain.

CITATION LIST

Patent Literature

Patent Literature 1: Japanese Laid-open Patent Publication No. 63-143830
Patent Literature 2: Japanese Laid-open Patent Publication No. 06-249791

SUMMARY OF INVENTION

Technical Problem

For example, in the dark-field inspection apparatuses having a dark-field condensing optical system, scanning with illumination laser light is performed, and scattered light is detected only when a defect is illuminated with a light source. Therefore, the detection signal is generally alternating current (pulse signal). However, the illumination spot is sufficiently larger than the target foreign substances, i.e., the extent to be inspected is widely illuminated. Incidentally, the mirror-finished wafers have the microroughness called haze, and the illumination with laser light causes light scattered by the haze. Since the scattered light caused by the haze generally has a sufficiently low frequency components compared with the signals from independent defects, the scattered light can be separated by circuit filtering. Nevertheless, pulse components caused by sensor-specific shot noise are superimposed on the low-frequency haze-scattered optical input. Therefore, when a wafer has a certain amount or more of haze, the shot noise as well as actual defects is counted as defects, so that measurement cannot be performed accurately. In addition, unless inspection is performed under an appropriate sensitivity condition corresponding to the haze level, there is a fear of causing saturation of the sensor output signal and a problem such as the impossibility of correct detection of the sizes of defects. Further, if an inspection condition for a new process step is set so as to avoid the above problem, the following problems will occur. That is, there is a problem that the operation of setting an inspection condition for a new process step so as to avoid the above problem relies on a heuristic method, and needs time to produce the inspection condition. In addition, because of the difference in the skill level among the operators who set the inspection condition, it is impossible to attain sufficient inspection performance in some cases. As explained above, the method of determining the inspection condition while measuring the signals has the problems of the necessity of time and the influence of the operator's discretion on the judgement as to validity of the sensitivity condition which is set as above.

An object of the present invention is to provide an inspection method and an inspection apparatus which can obtain in a short time a desirable inspection condition for inspection based on scattered light while suppressing the influence of the inspection operator's skill level.

Solution to Problem

According to an aspect of the present invention, an inspection apparatus is provided. The inspection apparatus includes: a stage which holds a specimen; an illumination optical system which illuminates a surface of the specimen held on the stage, with illumination light; a dark-field optical system which detects scattered light generated by the illumination light with which the specimen is illuminated; a photoelectric converter which converts the scattered light detected by the dark-field optical system, into an electric signal; an A/D converter which converts the electric signal obtained by conversion by the photoelectric converter, into a digital signal; a judgement unit which determines the dimension of a foreign substance on the surface of the specimen on the basis of the magnitude of the scattered light from the foreign substance; and a signal processor which determines an inspection condition by use of information on the scattered light from the specimen surface.

According to another aspect of the present invention, an inspection method is provided. The inspection method includes the steps of: detecting scattered light generated by illumination light with which a specimen is illuminated; converting the scattered light detected by the scattered-light detection optical system, into an electric signal; changing the electric signal obtained by the converting, into a digital signal; and determining a dimension of a foreign substance on a wafer surface on the basis of the magnitude of scattered light from the foreign substance. The inspection method further includes the step of using information on the scattered light from the surface of the specimen, for determination of a condition for detection of the scattered light.

The above aspects of the present invention will be further explained in detail below.

BRIEF DESCRIPTION OF DRAWINGS

FIGS. 2A and 2B are a diagram illustrating an illumination spot in the embodiment of the present invention.

DESCRIPTION OF EMBODIMENTS

Figure 1:
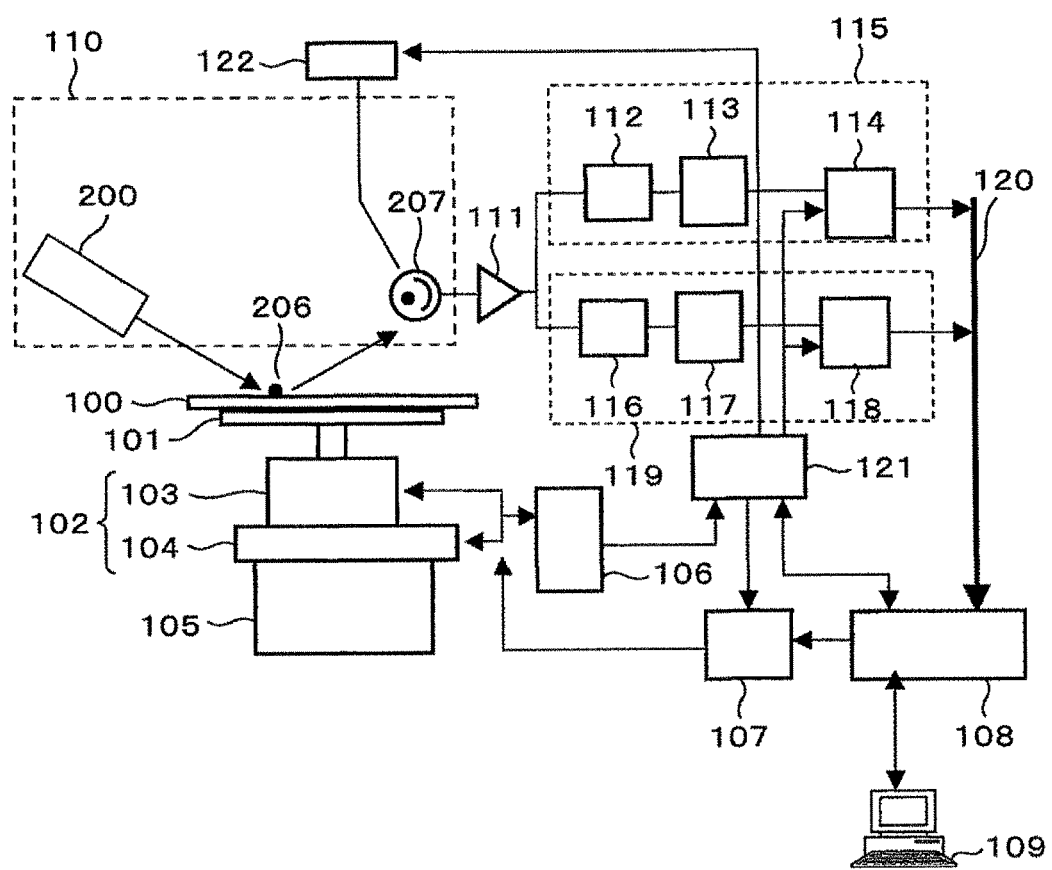
FIG. 1 is a diagram illustrating an outline of a constitution of an embodiment of the present invention.

Before the embodiments of the present invention are explained, an outline of the present invention is explained below.

According to the present invention, the fact that the (direct current) haze signal and the (pulsed) foreign-substance signal are each ratio of the magnitude of scattered light to the illumination power and are related to each other, and the physical phenomenon in which the magnitude of the shot noise increases statistically in proportion to the square root of the magnitude of the haze signal is utilized, and the limit of detection of a foreign substance and the maximum detectable size are predicted on the basis of haze information (surface roughness) acquired in advance, for preventing occurrence of artificial and maintaining high precision of detection.

A technique for realizing the above function is disclosed in this specification. According to the technique, the precision of the inspection for a foreign substance as a first inspection object to be measured can be maintained by using the haze as a second measured amount, and the performance limit can be easily achieved without trail and error.

1) For example, in consideration of the correlation between the roughness of the surface of the wafer and the artificial caused in the scattered light by microroughness on the wafer surface, the inspection apparatus directly measures the roughness information (haze) when the sensitivity to the foreign substance is set, automatically calculates an appropriate sensitivity in detection of a foreign substance and a range in which a foreign substance is detectable (the minimum size and the maximum size), and provides information to the operator.

2) Similarly, a great haze increases the direct-current component in the sensor and causes saturation. The inspection apparatus determines the maximum sensitivity which does not cause saturation, and provides information to the operator. In addition, in the case where the inspection is performed under a registered condition, the inspection apparatus avoids the saturation by automatically determining whether or not the haze is out of the range, before the inspection, and automatically shifting the sensitivity.

In the case where the haze of the wafer is small, the sensitivity can be raised to a level at which the saturation and the artificial defect are allowed. The inspection apparatus determines the maximum sensitivity which causes neither of the artificial defect and the saturation, in consideration of relationships between the haze, the sensitivity limit, and the saturation, and provides information to the operator.

The roughness of the wafer surface as the inspection object of the inspection apparatus according to the present invention is defined as the haze in the SEMI standard, has the effective height of approximately 0.1 to 10 nanometers and the pitch of the projection or recess of approximately 0.1 to 10 micrometers, and can be measured by an AFM (Atomic Force Microscope). However, the AFM can inspect only an extremely small area, and it is considered that inspection of the entire surface of a wafer by the AFM is not practicable.

On the other hand, according to the dark-field inspection method in which the wafer surface is illuminated with laser and scattered light is collected, scattered light correlating with the average height of the microroughness is generated in the laser illumination spot. Therefore, the above dark-field inspection method can obtain the haze as a signal having frequencies sufficiently lower than the LLS (localized Light Scatter) correlating with the rms value.

That is, the smooth surface and the rough surface are different in the haze. On the other hand, the detection limit of the inspection apparatus for the mirror-finished wafer and the like is noise. The noise corresponding to the detection limit is the sum of the circuit noise as a base and the noise generated by a detector which is several to ten or more times greater than the circuit noise. This noise has the shapes of isolated pulses which are generated randomly and independently of time and position, and cannot be discriminated from the LLS signals. In addition, it has been found out that the magnitude of the above noise corresponding to the detection limit correlates with the haze value. Although smaller defects can be detected when the haze value is smaller, currently, a process step of changing a parameter by the operator's experiences and trial and error is needed for determining the minimum detectable size.

However, conventionally, the relationship between the haze and the shot noise in the surface inspection is not considered.

The present inventors note that the DC (direct current) offset cancellation is insufficient in the case where the specimen has a great haze. Further, in the case where a wafer surface having a great haze is inspected by the technique for inspecting the surface of a semiconductor wafer by use of a dark-field system, the saturation of the sensor per se, instead of the amplifier range, is required to be considered. Since the above characteristics is directly related to the haze, it is necessary to lower the sensitivity to an appropriate level, for example, by changing the amount of light and the sensor bias condition. Specifically, the gain of the sensor per se is optimized by controlling the voltage applied to the photomultiplier. This operation sometimes reveals a signal saturated in the sensor.

The present invention provides an optimization technique which determines the optimum reduction of the sensitivity to signals saturated in the sensor.

The technical effect which is expected from the present invention is not to provide a means for optimally setting the sensitivity to independent defects as target objects on a surface having so great a haze that the signals of the independent defects are buried. Instead, the expected technical effect is to make an automatic correction within an allowed variation range of the haze for a wafer having such a haze as to affect the precision of detection. In addition, the expected technical effect in production of a condition is the ability to determine a condition which can bring out the best performance based on haze data obtained by photometry without taking time.

The present invention provides a technique which directly determines an appropriate sensitivity on the basis of the haze value.

Herein below, the embodiments of the present invention are explained with reference to drawings.

Embodiment 1

FIG. 1 is a diagram illustrating as the first embodiment an inspection apparatus for foreign substances and defects, which uses the inspection method for foreign substances and defects according to the present invention. The semiconductor wafer 100 as the inspection object is vacuum suctioned to the chuck 101. The chuck 101 is mounted on an inspection-object movement stage 102 and a Z stage 105, where the inspection-object movement stage 102 is constituted by a rotation stage 103 and a translation stage 104. The rotation stage 103 realizes a translation r, and the translation stage 104 realizes a rotation θ. The above stages are controlled through a stage control mechanism 107 on the basis of control signals from a host CPU 108 and a calculator 121. An illumination/detection optical system 110 includes a light source 200 and a sensor 207, and causes scattered light from a foreign substance or defect 206 on a wafer surface when the foreign substance or defect 206 is illuminated in an illumination spot by the light source. The sensor 207 detects the scattered light, converts the scattered light into an electric signal, and amplifies the electric signal with an amplifier 111. The scattered light detected by the amplifier 111 is split into a high-frequency foreign-substance/defect signal processing system 115 and a low-frequency haze-signal processing system 119.

In the high-frequency signal processing system 115 for high-frequency foreign substances, a high-pass filter 112 extracts pulse components, and an A/D converter a 113 converts the pulse components into a foreign-substance/defect digital signal. Thereafter, a foreign-substance/defect judgement system 114 synchronizes the foreign-substance/defect digital signal with foreign-substance/defect coordinates, and sends the dimensions and position of the foreign substance or defect to the host CPU 108 through a haze/defect data transfer system 120.

In the haze-signal processing system 119, a low-pass filter 116 extracts direct-current components and low-frequency components, and an A/D converter b 117 converts the direct-current components and low-frequency components into a haze digital signal. Thereafter, a haze judgement system 118 synchronizes the haze digital signal with haze coordinates, and sends the measured haze value to the host CPU 108 through the haze/foreign-substance/defect data transfer system 120. At this time, an inspection-coordinate detection system 106 detects the foreign-substance/defect coordinates of the foreign substance or defect under inspection, and the calculator 121 generates a coordinate synchronization signal for establishing synchronization with the coordinate position, and reports the current position to the host CPU 108. As explained above, when the entire wafer surface is scanned with the illumination spot, the dimensions and the positions of the foreign substances, defects, and the haze are determined, and inspection results are outputted to the input/output device 109, for example, in the form of a file of a map or a text, where the map indicates the distribution of the foreign substances and defects or the haze, and the text describes the position, the dimensions, and the type of each of the foreign substances and defects which are detected. In addition, conditions, commands, and the like for inspection of the foreign substances and defects are inputted through the input/output device 109, where the conditions include a sensitivity, a threshold, and the like, and the commands include a command to start the inspection, a command to perform an analysis or of the inspection results, a command to store the inspection results, and the like.

A sensor-sensitivity controller 122 makes of the sensitivity of the sensor for inspection of the entire wafer surface according to a condition which is set. Further, in order to acquire information for determining the sensor sensitivity before the start of the inspection of the entire wafer surface, the low-frequency haze-signal processing system 119 measures the haze value, and reports the measured haze value to the host CPU 108.

FIGS. 2A and 2B illustrate the illumination spot in the embodiment of the present invention. In addition, FIGS. 2A and 2B illustrate the illumination/detection optical system arranged above the semiconductor wafer 100. The light source 200 of the illumination light is a laser light source. An illumination beam 201 outputted from the light source 200 enters an illumination lens 202, and forms an illumination spot 203 having predetermined dimensions. The illumination light is, for example, p-polarized light, and the illumination/detection optical system is configured so that the illumination light is obliquely incident on the surface of the semiconductor wafer 100 as the inspection object at approximately the Blewster's angle for the crystalline Si. Since, in the above system, the illumination beam is fixed and the wafer is translated and rotated, the illumination beam moves through a spiral path on the wafer. The above trace is referred to as a spiral scan 208. At this time, the illumination spot 203 has approximately an elliptical shape, and has a major-axis component 204 in the radial direction r of the spiral scan 208 and a minor-axis component 205 in the radial direction θ of the spiral scan 208. Therefore, the illumination spot is redefined as the inside of a contour on which the illumination is $1/e^2$ of the illumination at the center of the illumination spot, where e is the natural logarithm. In order to prevent occurrence of a gap which is not illuminated with the illumination light in the spiral scan of the semiconductor wafer 100 and is not inspected, the illumination spot 203 are set so that a predetermined portion of each track in the spiral scan overlaps the next track. In addition, although the scan in the present embodiment is performed from the inner region to the outer region, the scan may be performed in the reverse direction. When the illumination spot produced by the illumination by the light source covers a foreign substance or defect 206 on the surface of the semiconductor wafer 100, scattered light is generated. The sensor 207 detects the scattered light through a condenser lens 209 in a light-receiving optical system, and converts the scattered light into an electric signal.

The magnitude of the scattered light being caused by a foreign substance and having dimensions smaller than the wavelength of the laser light with which the wafer is illuminated can be generally determined by the optical constants (refractive index and birefringence magnitude), the thickness of the thin film, the refractive index of the foreign substance, the dimensions of the foreign substance, the illumination angle in the detection optical system, the polarization direction, the arrangement of the optical receiver, and the analyzer. In most cases, the optical constants are determined by the material in the form of a film, and can be measured by using a well known method. The magnitude of the scattered light can be normalized to a ratio to the illumination power density (i.e., the illumination power per illumination area), and specifically to the quantity called BRDF (Bidirectional Reflectance Distribution Function), which can be calculated by simulation. Thus, the normalized magnitude of the scattered light does not depend on the illumination power or the illumination area.

Although the calculation result of the normalized magnitude of the scattered light is generally provided in the form of a table indicating the normalized ratio of the scattered light versus the size of the foreign substance. In the range of the sizes of the foreign substances sufficiently smaller than the measurement wavelength, it is possible to consider that the magnitude of the scattered light obeys the Rayleigh's Law, in $$Particle_{BRDF} = C_{c,k,n} \times r^6 \quad (eq. 1)$$

which the magnitude of the scattered light decreases in proportion to the sixth power of the size of the foreign substance. Therefore, the normalized ratio of the scattered light, $Particle_{BRDF}$, can be expressed as
where r is the diameter of the foreign substance.

In addition, the magnitude $P_{dp}$ of the scattered light entering the sensor can be expressed as $$P_{dp} \leq Particle_{BRDF} \times p/s \quad (eq. 2)$$

where p is the illumination power, and s is the illumination area.

On the other hand, in the case where the wafer surface has a haze (micro roughness), and illumination with sufficiently focused laser light causes uniform scattered light in the illuminated area, so that the detector detects an integrated magnitude of scattered light from each point.

The amount of light incident from the above haze can also be handled as a BRDF value independent of the sensor sensitivity or the illumination power, by normalizing the magnitude of the scattered light to the ratio to the illumination power. In the case where the illumination power p and the measured value of the haze, Meas Haze, which is measured through a limited NA in the entire solid angle through which the scattered light can be measured, are known in advance, the BRDF can be expressed as $$Haze_{BRDF} = K \times \frac{P_{dh}}{p} = K \times \frac{C * Meas\ Haze}{S_k * g_{(PMTHV)} * p} \quad (eq. 3)$$

where $S_k$ is the cathode radiant sensitivity of the sensor (i.e., the ratio of the current to the amount of the light incident on the photoelectric conversion surface), g (PMTHV) is the multiplication factor, $P_{dh}$ is the amount of light incident on the sensor (i.e., the magnitude of the scattered light from the haze), C is the conversion coefficient in the haze processing system, and K is an appropriate proportional constant. The sensor is a photomultiplier, and the multiplication factor can be varied with the applied voltage PMTHV.

Since C and $S_k$ are constants specific to the used sensor and the inspection apparatus, the formulas (eq. 3) indicates that the normalized haze value $Haze_{BRDF}$ can be calculated from the amount of the haze (Meas Haze) measured under a predetermined condition (that g(PMTHV) and p are known).

On the other hand, when the haze scattered light as the micro roughness on the wafer surface enters the sensor, the haze scattered light causes shot noise. When the magnitude of the shot noise becomes equivalent to the magnitude of the signal of the foreign substance, the size of the foreign substance becomes the detection limit of the patternless-wafer foreign-substance inspection apparatus. The magnitude of the noise is known to increase in proportion to the square root of the magnitude of the cathode current. In addition, the magnitude of the cathode current is proportional to the amount $P_{dh}$ of the light entering the sensor, and the amount $P_{dh}$ is proportional to the normalized haze amount $Haze_{BRDF}$. Therefore, the magnitude of the noise signal increases in proportion to the square root of the magnitude of the normalized haze amount $Haze_{BRDF}$.

Figure 3:
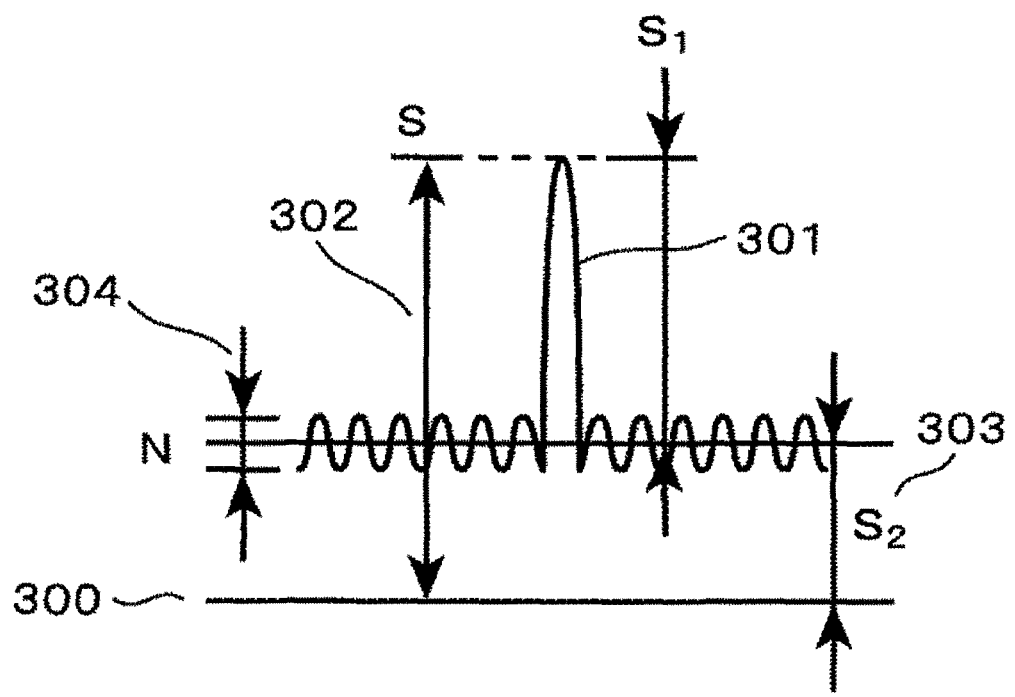
FIG. 3 is a diagram indicating a haze signal, a foreign-substance signal, and a waveform of shot noise in the embodiment of the present invention.

FIG. 3 is a diagram indicating a haze signal, a foreign-substance signal, and a waveform of shot noise in the embodiment of the present invention. FIG. 3 indicates signals detected when the inspection apparatus according to the present embodiment detects a defect on a wafer having a certain degree of roughness. The signals indicated in FIG. 3 are output signals of the amplifier 111 illustrated in FIG. 1, which are the signals in the stage preceding the independent extraction of the high-frequency components and the low-frequency components. In FIG. 3, the abscissa corresponds to time, and the ordinate corresponds to the magnitudes of the signals from the ground level. The detection signal 302 has the magnitude S, which is the sum of the magnitude S1 of the signal 301 from the foreign substance and the magnitude S2 of the haze signal 303, i.e., S=S1+S2. The foreign-substance signal 301 from the foreign substance becomes a pulse signal since the foreign-substance signal 301 is generated only while a spot is illuminated with the laser. In the range of the sizes of the foreign substances sufficiently smaller than the measurement wavelength, the magnitude S1 of the foreign-substance signal 301, i.e., the magnitude of the scattered light, is proportional to the sixth power of the size of the foreign substance, and is also proportional to the illumination power and the sensitivity of the sensor. On the other hand, the magnitude S2 of the haze signal 303 correlates with the surface roughness, and is proportional to the illumination power and the sensor sensitivity. Further, the shot noise 304, which is proportional to the square root of the above haze component, is superimposed on the above pulse component. The shot noise is also a pulse component. When the magnitude of the shot noise becomes equivalent to the magnitude of the foreign-substance signal from a foreign substance of the detection limit size, substances smaller than the detection limit size cannot be detected. That is, this is the detection limit. When the illumination power is fixed, the limit is determined by the magnitude of the haze regardlessly of the sensor sensitivity.

The shot noise which is caused when a wafer having a haze expressed by $Haze_{BRDF}$ is illuminated with the power p can be expressed by an amount Psn of the incident light equivalent to the noise level as $$P_{sn} = C_n \times (Haze_{BRDF} \times P)^{0.5} \quad (eq. 4)$$

where $C_n$ is an appropriate proportional constant.

On the other hand, the size of the foreign substance satisfying $P_{dp}=P_{sn}$ can be obtained from the equations (eq. 2) and (eq. 4) as $$P_{dp} = P_{sn} = C_n \times (Haze_{BRDF} \times p)^{0.5} = C_{o,k,n} \times r^6 \times p/s \quad \text{(eq. 5)}$$

$$r_{min} = \left(\frac{C_n}{C_{o,k,n}} \times \frac{s}{\sqrt{p}}\right)^{0.166} \times Haze_{BRDF}^{0.0833}$$

where $r_{min}$ is the size limit.

That is, when the value $Haze_{BRDF}$ can be obtained from the equation (eq. 3) under a certain condition, it is possible to predict the minimum detectable size of the foreign substance on the wafer from the equation (eq. 5).

Figure 4:
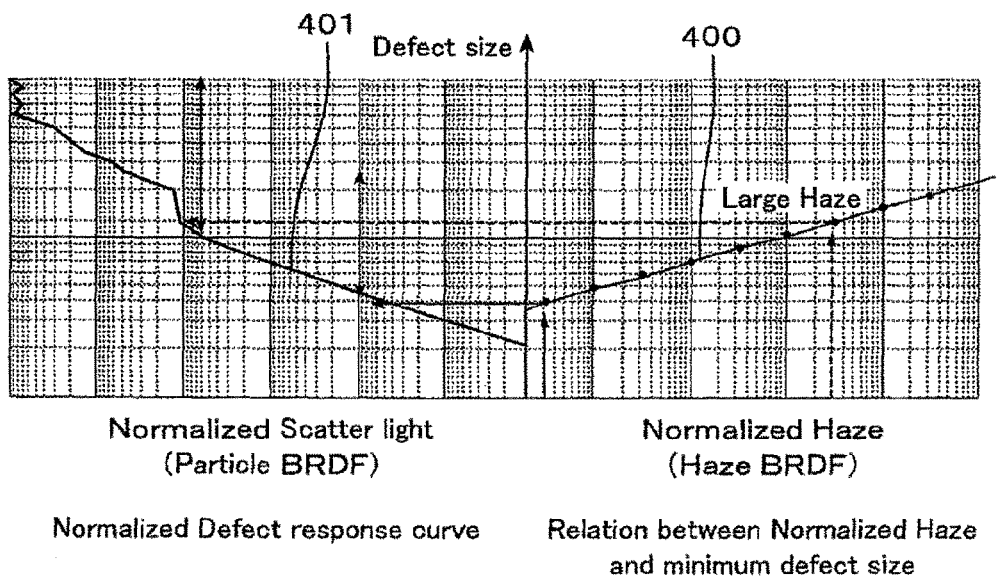
FIG. 4 is a diagram indicating a procedure for obtaining a sensitivity limit from a normalized haze value in the embodiment of the present invention.

FIG. 4 is a diagram indicating a procedure for obtaining a sensitivity limit from a normalized haze value in the embodiment of the present invention.

A graph 400 indicating a relationship between the minimum detectable size of the foreign substance and the normalized haze value is presented on the right side in FIG. 4. In the graph 400, the abscissa corresponds to the normalized haze value, and the ordinate corresponds to the size limit.

The signal including the haze indicated in FIG. 3 is extracted by the haze-signal processing system illustrated in FIG. 1, and the normalized haze value is calculated by the host CPU in accordance with the algorithm explained before. On the other hand, since the inspection apparatus holds the relationship indicated in the graph 400 in FIG. 4, for example, in a text data table in a storage unit provided in the inspection apparatus, it is possible to immediately obtain the minimum detectable size which can be detected under the aforementioned optical condition. Alternatively, the inspection apparatus may obtain the relationship indicated in the graph 400 in FIG. 4 by calculation as a value of a function.

In addition, a graph 401 indicating a relationship between the normalized amount of detected light and the size of the foreign substance is presented on the left side in FIG. 4. When the size limit is determined, the inspection apparatus can calculate a sensitivity condition most appropriate for the size which can be processed by the foreign-substance/defect signal processing system illustrated in FIG. 1, and control the sensor sensitivity.

Figure 5:
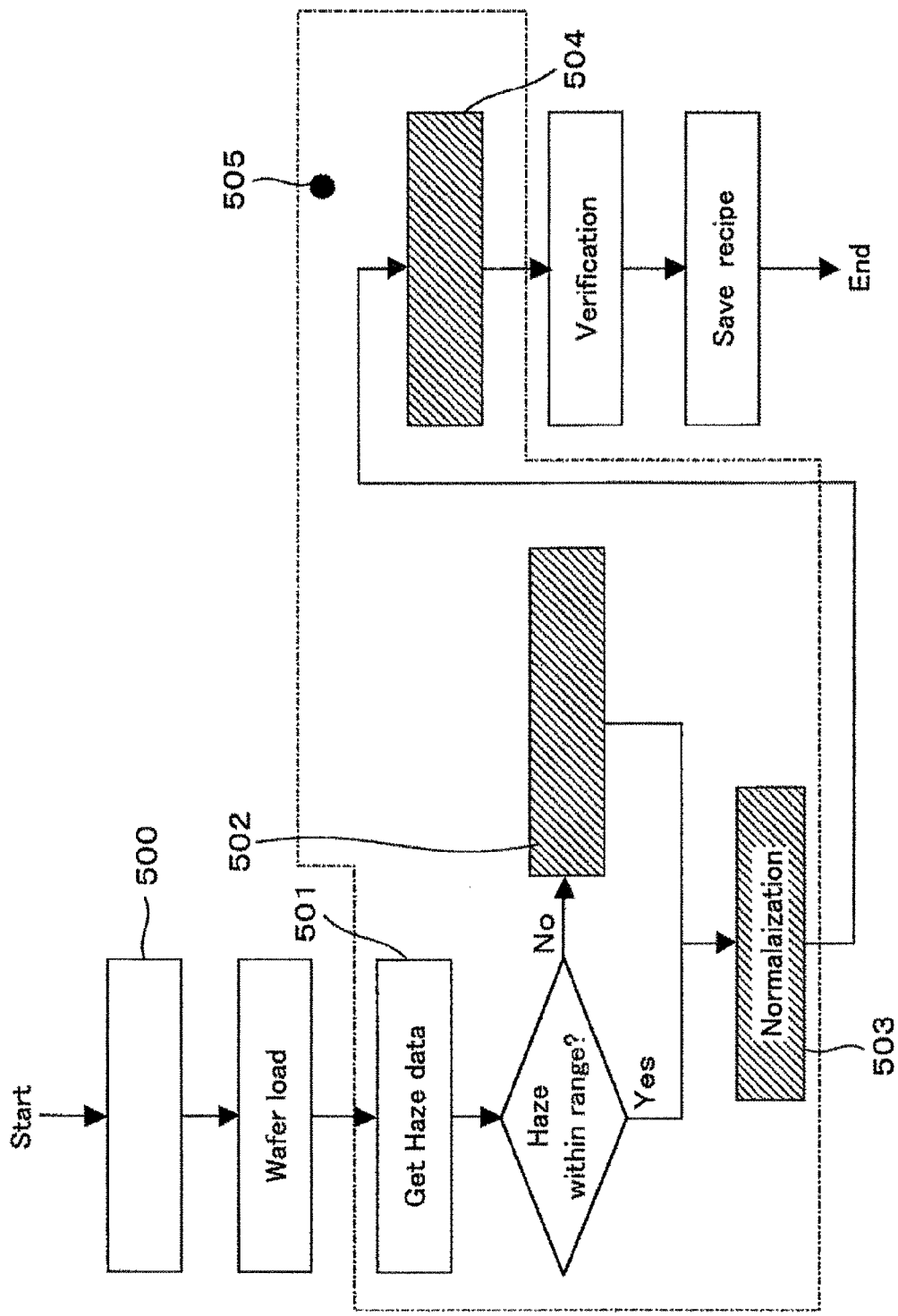
FIG. 5 is a diagram indicating a sequence of producing an inspection condition in the embodiment of present invention.

FIG. 5 is a diagram indicating a sequence of producing an inspection condition in the embodiment of present invention. An initial condition is set or selected through the input/output device 109, and the wafer as the inspection object is loaded (Wafer load). During conveyance of the wafer as the inspection object until the illumination spot reaches the initial inspection position, the haze premeasurement process 501 temporarily activates the haze-signal processing system 119 and performs photometry of a haze value (Get Haze data), and the normalized haze process 503 calculates a normalized haze value. At this time, when no valid haze value can be obtained under the initially set sensitivity condition (i.e., when no is determined in the judgement as to whether or not the haze value is within a range), the measurement-condition shift process 502 automatically adjusts the sensor sensitivity so that the haze value falls within the measurement range. Thereafter, the normalized haze process 503 calculates a normalized haze value (Normalization). That is, the sensitivity is automatically adjusted so as to be lowered when the measured haze value exceeds the upper limit, and to be raised when no haze value can be detected (by the sensor-sensitivity optimization process 504).

Before the start of the inspection, the sensor-sensitivity optimization process 505 prompts the input/output device 109 to whether to optimize the sensitivity on the basis of the normalized haze value. In the case where the optimization is performed, the minimum detection size is checked, and the initially inputted condition is finely controlled. Then, the entire wafer surface is inspected. Thereafter, verification is performed, and the condition is saved (Save recipe).

Figure 6:
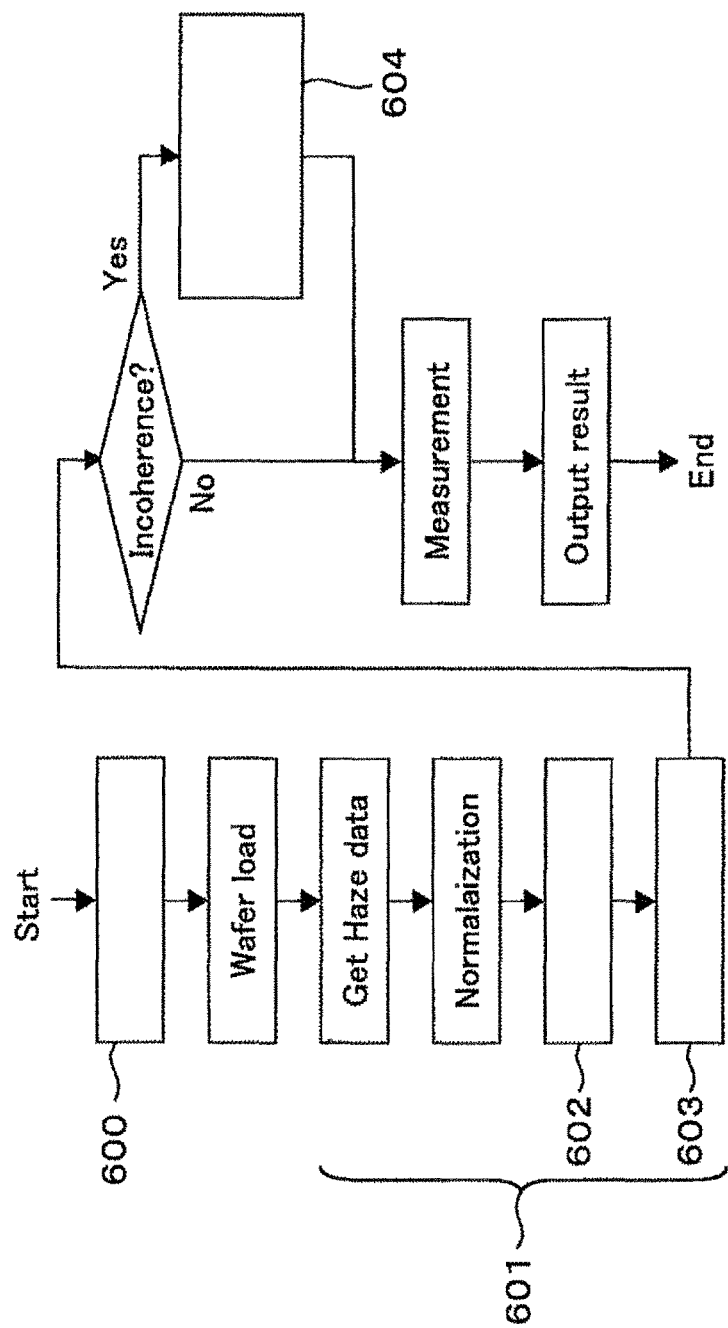
FIG. 6 is a diagram indicating a sequence of performing a normal inspection in the embodiment of present invention.

FIG. 6 is a diagram indicating a sequence of performing a normal inspection in the embodiment of present invention. An inspection condition 600 which is registered in advance is selected through the input/output device 109, and the inspection is started (in the measurement condition selection process 600). First, the wafer is loaded. Then, during conveyance of the wafer until the illumination spot reaches the initial inspection position, the process 601 for haze monitoring during normal inspection automatically perform, by using the respective functions constituting the inspection apparatus, collection of information for the normalized haze value (Get Haze data), calculation of the normalized haze value (Normalization), the process 602 for checking for saturation and detection limit, and the process 603 for judgement as to the validity of the inspection condition. When the measurement condition is determined to be inconsistent or incoherent (i.e., when yes is determined in the judgement as to the incoherence of the measurement condition), the process 604 for warning issuance and tentative sensitivity correction temporarily corrects the condition, performs inspection (Measurement), outputs a result, and completes the processing (End). Further, the inspection result and a warning indicating the tentative lowering of the sensitivity are outputted to the input/output device. The input/output device enables the selection of whether to activate the process 601 for haze monitoring during normal inspection, and the selection of whether a tentative condition change is permitted or only a warning is to be outputted.

Figure 7:
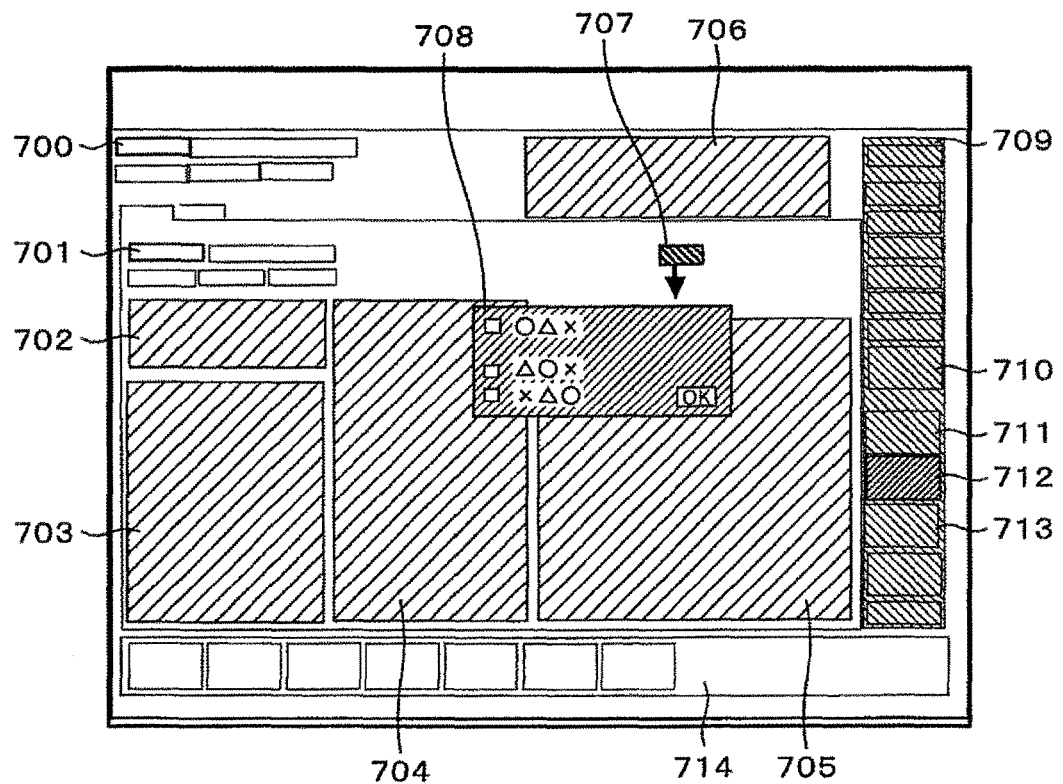
FIG. 7 is a diagram indicating a inspection-condition producing screen in the embodiment of present invention.

FIG. 7 is a diagram indicating an example of a screen for producing an inspection condition. The screen of FIG. 7 includes a menu button 700 for selection of an inspection condition, a menu button 701 for selection of a sensitivity condition, an area 702 for setting an illumination condition, an area 703 for setting a sensor sensitivity, an area 704 for setting a scanning condition or the like, an area 705 for setting a threshold and the size of the defect to be detected, an area 706 for setting an output display manner, an inspection area, and the like, a button 707 for setting a haze monitor function, a subarea 708 for displaying setting items for the haze monitor function, an area 709 for arrangement of command buttons, a button 710 for loading a wafer, a button 711 for starting the wafer inspection, a button 712 for performing optimization based on haze information, a button 713 for unloading the wafer, and an area 714 for arrangement of buttons for switching operational modes.

Illumination conditions 702 which are most appropriate for types and thicknesses of a thin film formed on the surface of the wafer to be inspected are registered in advance as initial conditions in the menu button 700 for selection of the inspection condition or in the menu button 701 for selection of the sensitivity condition. In the case where an inspection condition for the wafer to be inspected is newly produced, first, one of the registered initial conditions is selected in the menu button 700 or 701. At this time, the sensor sensitivity 703 is, for example, a sensitivity which is necessary for capturing a foreign substance of 0.1 micrometers on the wafer surface, and is a tentative value before optimization. The settings in the area 704 for setting a scanning condition and the area 706 for setting an output display manner, an inspection area, and the like are made as needed according to the purpose of the inspection regardlessly of the optimization of the sensitivity. In addition, the setting in the area 705 for setting the size of the defect is made according to the purpose of use after the optimization of the sensitivity is completed. In the case where optimization of the sensitivity based on the normalized haze value is performed, the subarea 708 for displaying setting items for the haze monitor function is displayed when the button 707 for setting the haze monitor function is pressed. When a switch "Haze pre-check enable", which is provided for activating the haze monitor function, is set to ON, the normalized haze value is measured and calculated, and the validity of the sensitivity condition is judged before the inspection is performed after the wafer is loaded. The items in the lower part of the subarea 708 are provided for enabling selection of the operation performed by the inspection apparatus when the validity of the sensitivity condition is judged to be N.G. in the case where the measurement is made in the normal mode. At this time, the selection is made between the operation of automatically shifting the sensitivity for the inspection and the operation of merely indicating a warning. Alternatively, it is possible to dispense with the button 707 for setting the haze monitor function, and display the subarea 708 for displaying setting items for the haze monitor function from the beginning. Since the necessity of the haze monitor function depends on the type of the wafer to be inspected, the items for the haze monitor function are arranged to be able to be independently registered for each condition. However, the items for the haze monitor function may be arranged to be able to be set for all inspection conditions in common. In the latter case, the subarea 708 for displaying setting items for the haze monitor function may be arranged in an initial setting area the access to which is specially authorized, an initialization file, or the like.

An example of manipulation on the screen of FIG. 7 for the operational flow of FIG. 5 is explained below. After the initial inspection condition is selected in the menu button 700 for selection of the inspection condition or the menu button 701 for selection of the sensitivity condition, the settings in the areas 704 to 706 are made as needed, and the wafer to be inspected is loaded by using the button 710 for loading a wafer. In the subarea 708 for displaying setting items for the haze monitor function, a checkbox "Effective" is checked. At this time, the sensitivity is not yet optimized, and the tentative sensitivity is given in the initial condition. When the wafer is loaded, the haze value is measured under the registered initial condition, and the normalized haze value is calculated. When the button 711 for starting the wafer inspection is pressed in the above situation, the inspection apparatus performs the inspection under the initial condition. When the button 712 for performing optimization based on haze information is pressed, the inspection apparatus performs the inspection with the sensitivity which is temporarily shifted upward or downward from the sensitivity set in the initial condition.

The amount of the above shift is such that the minimum detection size can maximally utilize the effective measurement range. However, it is possible to prompt input of a target size equal to or greater than the minimum detectable size by adding to the display area 708 a further item to be set, and realize such optimization that the size designated by the input enables the maximum utilization the effective measurement range. After the inspection is started by pressing the bottom 711 for starting the wafer inspection and is actually performed under the tentatively optimum condition corrected as above, the sensitivity condition and the inspection condition are newly saved. When the button 713 for unloading the wafer is pressed, the wafer is unloaded, and the operation for optimizing the sensitivity is completed.

Figure 8:
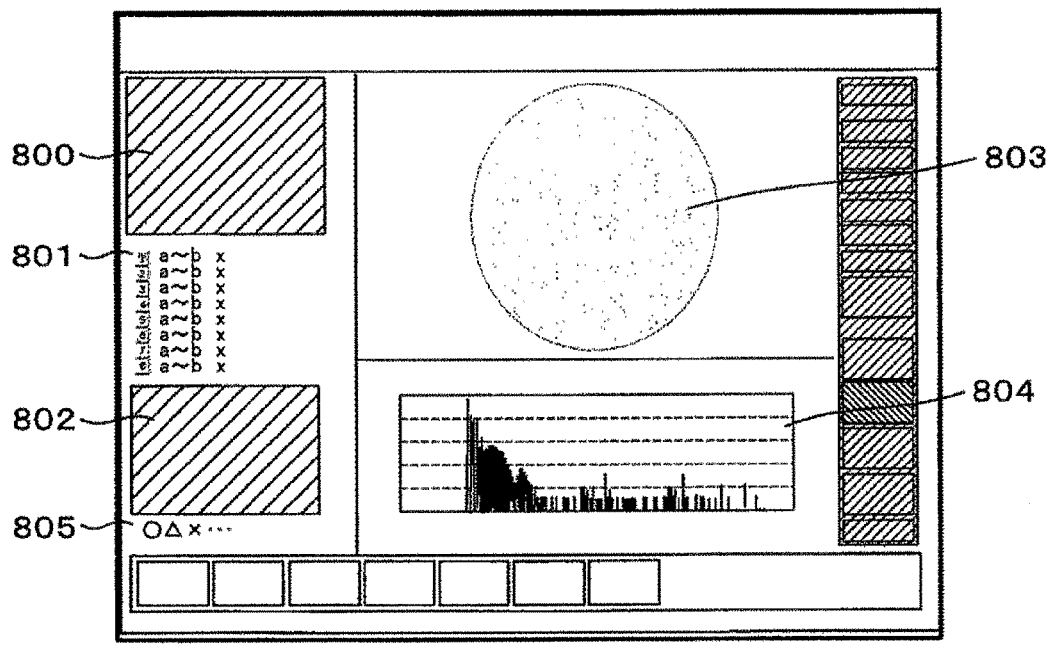
FIG. 8 is a diagram illustrating a warning indication, which is presented in a result of an inspection in the case where the haze monitor function is activated in the inspection and the validity of a measurement condition is determined to be N.G. in the inspection.

FIG. 8 is a diagram illustrating a warning indication which is presented in a result of an inspection in the case where the haze monitor function is activated in the inspection and the validity of a measurement condition is determined to be N.G. in the inspection. That is, the screen of FIG. 8 includes an area 800 for displaying a measurement condition, inspection information, and the like, an area 801 for displaying the number of detected defects for each defect size, an area 802 for displaying the haze value and the number of detected defects for each defect category, a defect map 803, a histogram 804 of the number of detected defects for each defect size, and a warning indication 805 for warning that the defect size is not accurately recognized. The screen of FIG. 8 is an example of a result of a wafer inspection displayed when the measurement condition under which the normalized haze value is measured is determined to be N.G. as a result of a validity judgement in the inspection, and the haze monitor function is activated in the inspection by the setting in the subarea 708 for displaying setting items for the haze monitor function, and the operation of the inspection apparatus is set to merely indicate a warning. In the example of FIG. 8, a result of measurement performed without correction of the sensitivity condition is displayed in the area 801 for displaying the number of detected defects for each defect size, and a warning 805 that the defect size is not accurately recognized is displayed. The information other than the warning is the same as the normal inspection result.

Figure 9:
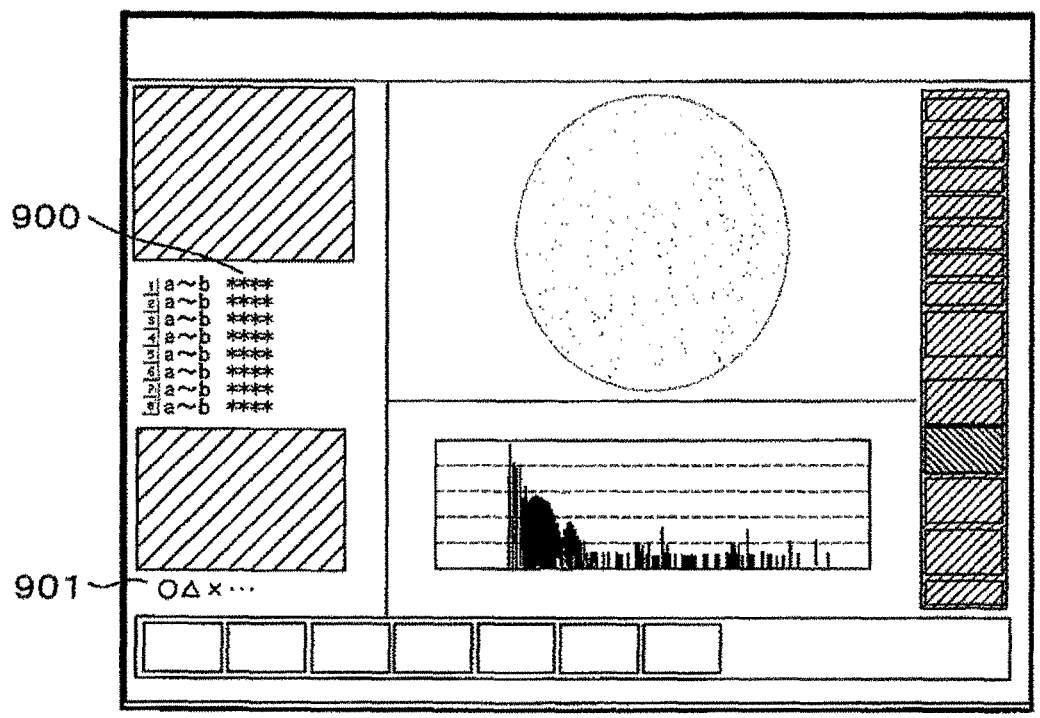
FIG. 9 is a diagram illustrating an indication of invalidness of a result with the minimum size which is presented as a result of an inspection in the case where the haze monitor function is activated and the sensitivity is automatically corrected after the validity of a measurement condition is determined to be N.G. in the inspection.

FIG. 9 is a diagram illustrating an indication of invalidness of a result with the minimum size which is presented as a result of an inspection in the case where the haze monitor function is activated in the inspection and the sensitivity is automatically corrected after the validity of a measurement condition is determined to be N.G. in the inspection. That is, the screen of FIG. 9 is an example of a result of a wafer inspection displayed when the measurement condition under which the normalized haze value is measured is determined to be N.G. as a result of a validity judgement in the inspection, in the case where the haze monitor function is activated in the inspection by the setting in the subarea 708 for displaying setting items for the haze monitor function, and the operation of the inspection apparatus is set to temporarily lower the sensitivity for performing the inspection. Since the minimum detection size is automatically changed, a special symbol such as the asterisk, instead of the number of detected defects, is indicated as a size-classified indication 900 out of the count range, and an indication 901 for warning that the sensitivity is automatically corrected before the measurement is also displayed.

Embodiment 2

Figure 10:
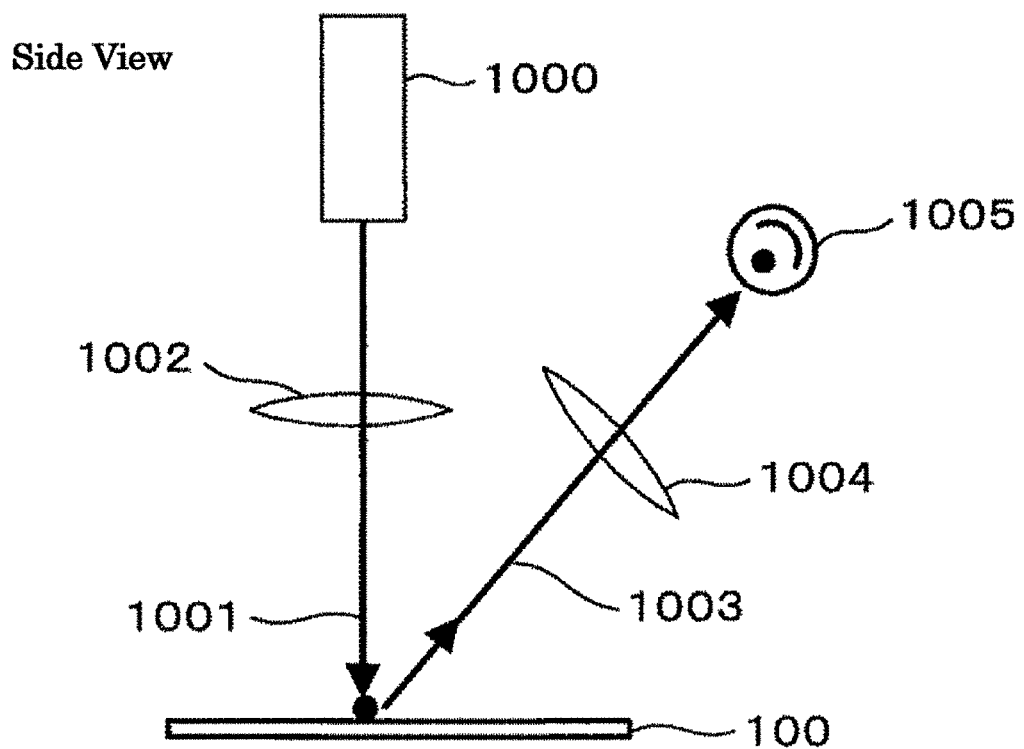
FIG. 10 is a diagram illustrating an outline of an optical system in the embodiment 2.

FIG. 10 is a diagram illustrating an outline of an optical system in the embodiment 2. In the embodiment 1, the illumination light is obliquely incident on the wafer 100. On the other hand, in the embodiment 2, an illumination beam 1001 from a laser light source 1000 is focused through an illumination lens 1002 onto a spot on the wafer 100, and the illumination light is vertically incident on the wafer 100. Scattered light 1003 from a foreign substance or defect is condensed by a condenser lens 1004, and lead to a sensor 1005. The angle at which the condenser lens 1004 in a light-receiving optical system is arranged may be different from the angle at which the light-receiving condenser lens 209 is arranged in the embodiment 1 illustrated in FIGS. 2A and B. Alternatively, the inspection apparatus in the embodiment 2 may have an optical-path switching mechanism which enables selection of one of the oblique down illumination and the vertical illumination, and a light-receiving optical system which enables parallel processing of both of the signals corresponding to the light-receiving condenser lens 209 collecting light scattered at low angles and the signals corresponding to the light-receiving condenser lens 1004 collecting light scattered at high angles.

The scanning of the inspection object may be the spiral scan realized by the rotation and translation of the inspection object, or by movement of the inspection object in the X- and Y-directions.

In either of the embodiments 1 and 2, a method and functions for measuring the haze value, obtaining the normalized haze value under a condition, and determining a size limit and an optimum condition enabling inspection of the size limit, on the basis of relationships between the normalized haze values and the size limits, before the wafer inspection, in accordance with an algorithm using the equations (eq. 1) to (eq. 5) as explained above, where the size limits are respectively specified for film types and optical conditions.

As explained above, in this specification, the inspection apparatuses are disclosed. The inspection apparatuses include: for example, a stage which holds a specimen; an illumination optical system which illuminates a surface of the specimen held on the stage, with illumination light; a dark-field optical system which detects scattered light generated by the illumination light with which the specimen is illuminated; a photoelectric converter which converts the scattered light detected by the dark-field optical system, into an electric signal; an A/D converter which converts the electric signal obtained by the conversion by the photoelectric converter, into a digital signal; and a judgement unit which determines the dimension of a foreign substance on the surface of the specimen on the basis of an magnitude of the scattered light from the foreign substance. When the inspection apparatuses determine a detection condition, optimization by use of information on the scattered light from the specimen surface is performed.

The inspection apparatus can acquire the scattered light from the specimen surface in advance of the inspection. Choices for optical systems, which are respectively most appropriate for types and thicknesses of films, are registered as initial conditions under which the scattered light from the specimen surface is acquired in advance. In addition, the inspection apparatuses make a selection of whether to perform optimization of condition setting by use of the information on the scattered light from the specimen surface.

In the above inspection apparatuses, the signal processor and the detection optical system acquiring the scattered light from the specimen surface before the inspection use the same construction as the signal processor and the detection optical system scanning the entire specimen surface for the condition of and foreign substance on the specimen surface. The signal processor and the detection optical system acquiring the scattered light from the specimen surface before the inspection are different, only in the inspection timing, from the signal processor and the detection optical system scanning the entire specimen surface for the condition of and foreign substance on the specimen surface. In addition, the inspection of the specimen is performed by performing partial sampling from least one point on the specimen before the start of the inspection of the entire inspection after the loading of the specimen on the stage. In the sampling, the sensor sensitivity is variably controlled so as to be changed stepwise from the initial condition until the measured value of the scattered light from the specimen surface falls within a desired range.

The inspection apparatuses can calculate the normalized haze value of the specimen on the basis of the acquired information on the scattered light from the specimen surface and the inspection condition, and can immediately determine the optimum condition and the minimum detectable size by automatic calculation. At this time, the optimum condition determined by the inspection apparatuses is displayed on the input/output device, so that it is possible to make a selection for making the optimum condition valid or invalid.

In the case where the inspection apparatuses perform the inspection under an already registered condition, the inspection apparatuses can determine, before the inspection, whether or not the condition under which the inspection is to be performed is appropriate for inspection of the specimen. When the measured scattered light from the specimen surface is out of a range which is preset in a condition, the inspection apparatuses determines that the condition under which the inspection is to be performed is inappropriate.

The operations which the inspection apparatuses can perform when the inappropriateness is determined before the inspection include:

1) To indicate, in the inspection result, a warning that the magnitude of the scattered light from the specimen surface is out of the range; and 2) To automatically lower the sensitivity so that the condition becomes optimum in a range which is separately preset, and perform the inspection. In the case of the operation 2), the inspection apparatuses indicate, in the inspection result, the fact that the magnitude of the scattered light from the specimen surface is out of the range and the sensitivity is automatically corrected. Further, when the magnitude of the scattered light from the specimen surface is out of a correctable range, the inspection apparatuses do not perform the correction, and indicates a warning "Abnormal Magnitude of Scattered Light from Specimen Surface".

The inspection apparatuses are configured to enable selection of one of the operations 1) and 2) through the input/output device.

In an inspection apparatus, the specimen as the inspection object is a patternless, mirror-finished, bare silicon wafer or a patternless, bare silicon wafer with a deposited film. The wafer is inspected for a localized defect which exists on the wafer surface and causes scattered light when the defect is illuminated with laser light, and the localized defect is a foreign substance, a scratch, a stain, a crystalline defect existing on the wafer surface, or the like. The inspection apparatuses may determine the size of the detected defect by making conversion to a unit for sensitivity calibration based on a standard particle size, and output the position and the number of defects on the wafer.

According to the present invention, a method for optically inspecting the surface of a wafer surface for a foreign substance is disclosed. The method uses: a stage which holds a specimen; an illumination optical system which illuminates a surface of a specimen held on the stage, with illumination light; a scattered-light detection optical system which detects scattered light generated by the illumination light with which the specimen is illuminated; a photoelectric converter which converts the scattered light detected by the scattered-light detection optical system, into an electric signal; and an A/D converter which converts the electric signal obtained by conversion by the photoelectric converter, into a digital signal. In the method, the size of a foreign substance on the wafer surface is determined on the basis of the magnitude of the scattered light from the foreign substance. In addition, the method uses a function of optimizing the detection condition by using information on the scattered light from the wafer surface (haze) when the detection condition is determined.

In addition, in the above method, the normalized haze value of the wafer is calculated on the basis of acquired haze data and the inspection condition, and the optimum condition and the minimum detectable size are automatically and immediately calculated and determined by an inspection apparatus.

An embodiment of the present invention may have one or more of the following advantages:

The first advantage that the precision of the size of the foreign substance can be secured when the surface condition varies within an allowable range.

The second advantage that inspection for foreign substances having a size equal to or greater than a certain level can be performed when the surface condition varies within an allowable range.

The third advantage that the performance at a level equal to or higher than a certain level can be attained in production of the condition without depending on the skill level of the operator.

The fourth advantage that the optimum condition can be produced in a short time.

Although the embodiments of the present invention are explained above, the present invention is not limited to the explained embodiments, and the explained embodiments can be modified in various ways within the scope of the present invention.

REFERENCE SIGNS LIST

100: semiconductor wafer
101: chuck
102: inspection-object movement stage
103: rotation stage
104: translation stage
105: Z stage
106: inspection-coordinate detection system
107: stage control mechanism
108: host CPU
109: input/output device
110: illumination/detection optical system
111: amplifier
112: high-pass filter
113: A/D converter a
114: foreign-substance/defect judgement system
115: high-frequency foreign-substance/defect signal processing system
116: low-pass filter
117: A/D converter b
118: haze judgement system
119: haze-signal processing system
120: haze/foreign-substance/defect data transfer system 120
121: calculator
122: sensor-sensitivity controller
200,1000: laser light source
201,1001: illumination beam
202,1002: illumination lens
203: illumination spot
204: major-axis component of illumination spot
205: minor-axis component of illumination spot
206: foreign substance or defect
207, 1005: sensor
208: spiral scan
209,1004: condenser lens in light-receiving optical system
300: ground level
301: waveform of signal from foreign substance
302: waveform of detection signal
303: waveform of haze signal
304: waveform of shot noise
400: graph indicating relationship between minimum detectable size of foreign substance and normalized haze value
401: graph indicating relationship between size of foreign substance and normalized amount of detected light
500: process for selecting initial condition (during production of new condition)
501: haze premeasurement process
502: process for shifting inspection condition
503: process for normalized haze value
504: process for optimizing sensor sensitivity
505: process for optimizing sensitivity in detection of defect based on haze information
600: process for selecting measurement condition
601: process for monitoring haze during normal inspection
602: process for checking for saturation and detection limit
603: process for judgement as to validity of inspection condition
604: process for warning issuance and tentative correction of sensitivity
700: menu button for selection of inspection condition
701: menu button for selection of sensitivity condition
702: area for setting an illumination condition
703: area for setting sensor sensitivity
704: area for setting scanning condition or the like
705: area for setting threshold and size of defect to be detected
706: area for setting output display manner, inspection area, and the like
707: button for setting haze monitor function
708: subarea for displaying setting items for haze monitor function
709: area for arrangement of command buttons
710: button for loading wafer
711: button for starting wafer inspection
712: button for performing optimization based on haze information
713: button for unloading the wafer
714: area for arrangement of buttons for switching operational modes
800: area for displaying measurement condition, inspection information, and the like
801: area for displaying the number of detected defects for each defect size
802: area for displaying haze value and the number of detected defects for each defect category
803: defect map
804: histogram of the number of detected defects for each defect size
805: indication of warning that defect size is not accurately recognized
900: size classified indication when measurement is performed after sensitivity is automatically lowered
901: indication of warning that measurement is performed after automatic correction of sensitivity
1003: scattered light

The invention claimed is:

1. An inspection apparatus comprising:
an illumination system configured to supply a sample with a light;
a detection system configured to detect the light from the sample;
a processing system configured to acquire a predetermined frequency component which is an electrical signal from the detection system, wherein the predetermined frequency component is lower than a frequency component indicating an anomaly on the sample.

2. The inspection apparatus according to claim 1, wherein the predetermined frequency component is a haze signal.

3. The inspection apparatus according to claim 2, wherein the processing system is configured to:

acquire a normalized haze signal from the haze signal, and acquire the size range of the anomaly based on the normalized haze signal.

4. The inspection apparatus according to claim 3, wherein the processing system is configured to acquire a detection sensitivity for an inspection based on the size range of the anomaly.

5. The inspection apparatus according to claim 4, wherein the processing system is configured to acquire the normalized haze signal between a loading of the sample and the inspection.

6. The inspection apparatus according to claim 1, wherein the processing system is configured to:

acquire a normalized predetermined frequency component from the predetermined frequency component, and acquire the size range of the anomaly based on the normalized predetermined frequency component.

7. The inspection apparatus according to claim 6, wherein the processing system is configured to acquire the normalized predetermined frequency component between the loading of the sample and the inspection.

8. The inspection apparatus according to claim 1, wherein the processing system is configured to acquire a detection sensitivity for the inspection based on the size range of the anomaly.

9. An inspection method comprising steps of:

supplying, using an illumination system, a sample with a light;

detecting, using a detection system, light from the sample;

acquiring, using a processing system:

a predetermined frequency component which is lower than a frequency component indicating an anomaly on the sample, and a size range of the anomaly on based on the predetermined frequency component.

10. The inspection method according to claim 9, wherein the predetermined frequency component is a haze signal.

11. The inspection method according to claim 10, further comprising a step of acquiring, using the processing system, a normalized haze signal from the haze signal, and the size range of the anomaly based on the normalized haze signal.

12. The inspection method according to claim 11, further comprising a step of acquiring, using the processing system, a detection sensitivity for an inspection on based on the size range of the anomaly.

13. The inspection method according to claim 11, further comprising a step of acquiring, using the processing system, the normalized haze signal between a loading of the sample and the inspection.

14. The inspection method according to claim 9, further comprising a step of acquiring, using the processing system, a normalized predetermined frequency component from the predetermined frequency component.

15. The inspection method according to claim 14, further comprising a step of acquiring, using the processing system, the normalized predetermined frequency component between the loading of the sample and the inspection.

16. The inspection method according to claim 9, further comprising a step of acquiring, using the processing system, a detection sensitivity for the inspection based on the size range of the anomaly.

* * * * *